United States Patent
Mais et al.

(10) Patent No.: US 6,441,171 B1
(45) Date of Patent: Aug. 27, 2002

(54) METHOD FOR THE PRODUCTION OF 4,6-DICHLOROPYRIMIDINE WITH THE AID OF PHOSGENE

(75) Inventors: Franz-Josef Mais, Düsseldorf; Günther Cramm, Leverkusen; Alexander Klausener, Pulheim; Guido Steffan, Odenthal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/048,087

(22) PCT Filed: Jul. 17, 2000

(86) PCT No.: PCT/EP00/06805

§ 371 (c)(1),
(2), (4) Date: Jan. 24, 2002

(87) PCT Pub. No.: WO01/09105

PCT Pub. Date: Feb. 8, 2001

(30) Foreign Application Priority Data

Jul. 28, 1999 (DE) .......................................... 199 35 322

(51) Int. Cl.$^7$ ............................................. C07D 239/30
(52) U.S. Cl. ....................................................... 544/334
(58) Field of Search .......................................... 544/334

(56) References Cited

U.S. PATENT DOCUMENTS 5,677,453 A    10/1997    Cramm et al. .............. 544/334

FOREIGN PATENT DOCUMENTS

| EP | 0 697 406 | 2/1996 |
| EP | 0 745 593 | 12/1996 |
| GB | 2325224 | 11/1998 |
| WO | 95/29166 | 11/1995 |
| WO | 96/23776 | 8/1996 |

OTHER PUBLICATIONS

"Chlorination of Pyrimidines", Research Disclosure, GB, Industrial Opportunities Ltd., Havant, Nr. 391, Nov. 1, 1996, Seiten 690–691, XP000680903.

*Primary Examiner*—John M. Ford
(74) *Attorney, Agent, or Firm*—Joseph C. Gil; Richard E. L. Henderson

(57) ABSTRACT

The invention relates to a method for the preparation of 4,6-dichloropyrimidine by reacting 4-chloro-6-methoxypyrimidine with phosgene as chlorinating agent in the presence of a nitrogen-containing auxiliary.

8 Claims, No Drawings

METHOD FOR THE PRODUCTION OF 4,6-DICHLOROPYRIMIDINE WITH THE AID OF PHOSGENE

The present invention relates to a method for the preparation of 4,6-dichloropyrimidine from 4-chloro-6-methoxypyrimidine. 4,6-Dichloropyrimidine is a valuable intermediate for the preparation of crop protection agents.

A number of methods for preparing 4,6-dichloropyrimidine are known, see, for example, WO96/23776, EP-A-697 406, EP-A-745 593, WO 95/29166, DE-A-195 31 299 and GB 2 325 224. However, these methods always start from 4,6-dihydroxypyrimidine.

It is also known (see Res. Discl. n 391, 690–691 (1996)), that 4,6-dichloropyrimidine can be obtained by reaction of 4-chloro-6-methoxypyrimidine with a chlorinating reagent of the formula $R_3PCl_2$. The chlorinating reagent can be employed as such or be prepared in situ from a compound of the formula $R_3P=O$ and phosgene. This reference suggests that 4-chloro-6-methoxypyrimidine does not react with phosgene alone in the desired manner.

A method for the preparation of 4,6-dichloropyrimidine has now been found and is characterized in that 4-chloro-6-methoxypyrimidine is reacted with phosgene as chlorinating agent in the presence of nitrogen-containing auxiliaries.

The method according to the invention can be carried out in a solvent (for details, see below) or in the melt. The procedure in a solvent is preferred.

Examples of suitable nitrogen-containing auxiliaries are nitrogen-containing bases, for example amines of the formula $R^1R^2R^3N$ (in which $R^1$, $R^2$ and $R^3$ can denote independently of one another in each case for $C_1$–$C_{10}$-alkyl, $C_6$–$C_{10}$-aryl, $C_5$–$C_9$-heteroaryl with 1 to 3 heteroatoms from the group of N, O and S or $C_6$–$C_{10}$-aryl-$C_1$–$C_6$-alkyl) or unsaturated or saturated cyclic amines with 1 to 2 nitrogen atoms and from 5 to 11 carbon atoms, it being possible for the cyclic amines optionally to be substituted once to 3 times by $C_1$–$C_{10}$-alkyl. Examples of such amines are: triethylamine, N,N-diethylaniline, N,N-dimethylaniline, diisopropylethylamine, 4-(N,N-dimethylamino)pyridine (DMAP), $C_1$–$C_2$-alkyl-mono- or -dialkylated pyridines, morpholine, imidazole, triazole, 1,5-diazabicyclo[4.3.0]non-5-ene (DBN), 1,8-diazabicyclo[5.4.0]undec-7-ene (DBU) and piperidine. It is furthermore possible to employ as nitrogen-containing auxiliaries amides and ureas, which can also be used as solvents. Examples are: N,N-dimethylformamide, N,N-dimethylacetamide, N-methylpyrrolidone, tetramethylurea and cyclic ureas such as 1,3-dimethyimidazolidin-2-one (DMEU) and 1,3-dimethyltetrahydro-2(1H)-pyrimidinone (DMPH).

In general, at least 1 mol of phosgene is employed per mole of 4-chloro-6-methoxypyrimidine in the method according to the invention. This amount is preferably 1.05 to 20 mol, particularly preferably 1.1 to 10 mol.

The amount of nitrogen-containing auxiliaries can be varied within a wide range. Smaller amounts, for example those below 1 mol per mole of 4-chloro-6-methoxypyrimidine can be employed, for example, if the nitrogen-containing auxiliary is intended to be used as catalyst. Larger amounts, for example those of more than 1.5 mol per mole of 4-chloro-6-methoxypyrimidine can be employed if it is wished to employ the nitrogen-containing auxiliary both as catalyst and as solvent. For example, the amount of nitrogen-containing auxiliary can be between 0.001 and 25 mol, preferably between 0.01 and 15 mol, in each case based on 4-chloro-6-methoxypyrimidine. Amounts in the range from 0.01 to 0.5 mol per mole of 4-chloro-6-methoxypyrimidine are particularly preferred on use with the nitrogen-containing auxiliary as catalyst.

If it is wished to have solvents present, solvents which are suitable in principle are those which do not have adverse effects on the reaction to be carried out. Examples are aliphatic solvents such as alkanes, cycloalkanes and halogenoalkanes, aromatic solvents such as benzene, xylenes, toluene, chlorobenzenes, benzotrifluorides, p-chlorobenzotrifluoride and anisole, it being possible for the aliphatic and aromatic solvents to be further substituted where appropriate, nitriles such as acetonitrile and benzonitrile, N-containing solvents such as N,N-dimethylformamide, N,N-dimethylacetamide, lactams and cyclic ureas and ethers and polyethers of a wide variety of types.

The method according to the invention can be carried out for example at temperatures in the range from 0 to 200° C., preferably at 20 to 150° C., particularly preferably at 40 to 120° C. The pressure is not critical. It is possible to operate, for example, at 0.1 to 50 bar, preferably at 0.5 to 5 bar. Atmospheric pressure is particularly preferred.

The method according to the invention can be carried out in various embodiments, for example batchwise, semibatchwise, semicontinuously or continuously. One possible procedure is as follows: gaseous phosgene is passed into 4-chloro-6-methoxypyrimidine mixed with a nitrogen-containing auxiliary, where appropriate together with a solvent.

Another variant is to add phosgene in liquid form or dissolved in a solvent. It is moreover possible to add all the phosgene immediately at the start of the reaction or meter it distributed over a certain period.

The reaction mixture present after the reaction can be worked up, for example, by initially removing excess phosgene from the mixture by blowing out and/or partial distillation, and distilling the remaining reaction mixture.

If water-soluble auxiliaries have been employed, it is beneficial first to add water to the reaction mixture and, after the auxiliaries have been washed out and after the solvent has been distilled out, to distill or crystallize the remaining product.

Another generally advantageous variant consists of working up by extraction. On suitable choice of the combination of nitrogen-containing auxiliary with the solvent, in the simplest case N,N-dimethylformamide as nitrogen-containing auxiliary and xylene as solvent, the reaction mixture separates into two phases. The 4,6-dichloropyrimidine-containing xylene phase can then be separated off, and the N,N-dimethylformamide phase can be extracted one or more times more with xylene. The combined xylene phases can then be distilled.

It is also possible to carry out the reaction according to the invention only in the presence of a nitrogen-containing auxiliary and then to extract the resulting reaction mixture with a suitable solvent, for example aliphatic or aromatic hydrocarbons such as hexane, isooctane, methylcyclohexane, toluene, xylene, decalin, tetralin or hydrocarbon mixtures.

The method according to the invention is exceptionally surprising in the light of the reference Res. Discl. loc. cit. Although phosgene is mentioned as chlorinating agent therein, it is only for in situ generation of triorganodichlorophosphorane. Direct reaction of 4-chloro-6-methoxypyrimidine with phosgene is not mentioned.

The method according to the invention allows 4,6-dichloropyrimidine to be prepared in a simple manner and in good yields and without the use of phosphorus-containing chlorinating agents.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used.

EXAMPLES

Example 1

14.5 g of 4-chloro-6-methoxypyrimidine and a mixture of 75 ml of N,N-dimethylformamide and 75 ml of xylene were put into a stirred vessel and heated with stirring to 130 to 135° C., and then 99.9 g of gaseous phosgene were passed in at a constant rate over the course of 3 hours. Phosgene residues were then blown out with nitrogen for 3.5 hours. After cooling, 159.7 g of a two-phase reaction mixture were obtained. Phase separation resulted in 60.8 g of upper, clear xylene phase and 90.7 g of black lower N,N-dimethylformamide phase (remainder: loss on phase separation).

The HPLC contents were 15.57% of 4,6-dichloropyrimidine in the xylene phase and 5.38% in the N,N-dimethylformamide phase. This corresponds to yields of 63.45% 4,6-dichloropyrimidine in the xylene phase and 32.75% in the N,N-dimethylformamide phase, that is to say a total of 96.3% 4,6-dichloropyrimidine. 4-Chloro-6-methoxypyrimidine was undetectable in both phases.

Example 2

21.68 g of 4-chloro-6-methoxypyrimidine, 129 g of xylene and 36.35 g of N,N-dimethylaniline were put into a stirred vessel and heated with stirring to 105° C. At this temperature, 76 g of phosgene were passed in at a constant rate over the course of 3.5 hours. Excess phosgene was then blown out with nitrogen. After cooling, a two-phase mixture was obtained. The weight of upper, xylene-rich phase was 135.12 g, and the lower N,N-dimethylaniline-rich phase weighed 37.1 g.

HPLC analysis showed that the upper phase contained 0.22% 4-chloro-6-hydroxypyrimidine, 0.66% 4-chloro-6-methoxypyrimidine and 13.05% 4,6-dichloropyrimidine. The lower phase contained 0.5% 4-chloro-6-hydroxypyrimidine and 5.6% 4,6-dichloropyrimidine. This corresponds to a yield of 4,6-dichloropyrimidine of 88.2% based on 4-chloro-6-methoxypyrimidine employed.

What is claimed is:

1. A method for the preparation of 4,6-dichloropyrimidine comprising reacting 4-chloro-6-methoxypyrimidine with phosgene as chlorinating agent in the presence of a nitrogen-containing auxiliary.

2. The method according to claim 1 wherein the nitrogen-containing auxiliary is (i) an amine of the formula $R^1R^2R^3N$ in which $R^1$, $R^2$, and $R^3$ denote independently of one another $C_1$–$C_{10}$-alkyl, $C_6$–$C_{10}$-aryl, $C_5$–$C_9$-heteroaryl having 1 to 3 heteroatoms selected from the group consisting of N, O, and S, or $C_6$–$C_{10}$-aryl-$C_1$–$C_6$-alkyl, (ii) an unsaturated or saturated cyclic amine having 1 to 2 nitrogen atoms and from 5 to 11 carbon atoms, (iii) an amide, or (iv) a urea.

3. The method according to claim 1 wherein at least 1 mol of phosgene is employed per mole of 4-chloro-6-methoxypyrimidine.

4. The method according to claim 1 wherein the molar ratio of phosgene to 4-chloro-6-methoxypyrimidine is 1.05:1 to 20:1.

5. The method according to claim 1 wherein 0.001 to 25 mol of the nitrogen-containing auxiliary are employed per mole of 4-chloro-6-methoxypyrimidine.

6. The method according to claim 1 carried out in the presence of a solvent.

7. The method according to claim 6 wherein the solvent is an aliphatic solvent, an aromatic solvent, a nitrile, an N-containing solvent, an ether, or a polyether.

8. The method according to claim 1 carried out at temperatures in the range from 0 to 200° C. and pressures in the range from 0.1 to 50 bar.

* * * * *